(12) United States Patent
Quan et al.

(10) Patent No.: US 8,668,916 B2
(45) Date of Patent: Mar. 11, 2014

(54) HIPE-GELATION PROCESS FOR MAKING HIGHLY CONCENTRATED, SPHERICAL BIOPOLYMER GEL PARTICLE SUSPENSIONS

(75) Inventors: Congling Quan, Woodbridge, CT (US); Teanoosh Moaddel, Watertown, CT (US); Badreddine Ahtchi-Ali, Newtown, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 504 days.

(21) Appl. No.: 12/889,657

(22) Filed: Sep. 24, 2010

(65) Prior Publication Data

US 2012/0077881 A1    Mar. 29, 2012

(51) Int. Cl.
  *A61K 8/02*     (2006.01)
(52) U.S. Cl.
  USPC ........................................ 424/401; 424/1.25
(58) Field of Classification Search
  USPC .................................................. 424/401, 1.25
  See application file for complete search history.

(56) References Cited

U.S. PATENT DOCUMENTS

| | | | |
|---|---|---|---|
| 3,901,678 A * | 8/1975 | Fischer | 504/230 |
| 3,959,251 A | 5/1976 | Porath et al. | |
| 3,969,087 A | 7/1976 | Saito et al. | 44/7 |
| 4,480,089 A | 10/1984 | Chen et al. | 536/56 |
| 4,790,961 A | 12/1988 | Weiss et al. | 260/376 |
| 5,106,609 A | 4/1992 | Bolich, Jr. et al. | 424/70 |
| 5,151,451 A | 9/1992 | Brown et al. | 514/773 |
| 5,189,070 A * | 2/1993 | Brownscombe et al. | 521/64 |
| 5,215,733 A | 6/1993 | Potter | 423/338 |
| 5,250,640 A | 10/1993 | Irie et al. | 526/88 |
| 5,623,017 A | 4/1997 | Hill | 524/860 |
| 5,654,362 A | 8/1997 | Schulz, Jr. | 524/862 |
| 5,700,452 A | 12/1997 | Deckner et al. | |
| 5,738,897 A | 4/1998 | Gidley et al. | 426/573 |
| 5,773,564 A | 6/1998 | Sikes | 528/363 |
| 5,880,210 A | 3/1999 | Schulz, Jr. | 524/73 |
| 5,889,108 A | 3/1999 | Zhang | 524/862 |
| 5,929,164 A | 7/1999 | Zhang | 524/862 |
| 6,017,546 A | 1/2000 | Glover | 424/401 |
| 6,048,908 A * | 4/2000 | Kitagawa | 521/56 |
| 6,106,847 A | 8/2000 | Ferrero et al. | 424/401 |
| 6,262,170 B1 | 7/2001 | Kilgour et al. | 524/731 |
| 6,329,331 B1 | 12/2001 | Aronson et al. | 510/130 |
| 6,338,858 B1 | 1/2002 | Dupuis et al. | 424/486 |
| 6,355,724 B1 | 3/2002 | LeGrow et al. | 524/731 |
| 6,423,322 B1 | 7/2002 | Fry | 424/401 |
| 6,673,371 B2 | 1/2004 | Brown et al. | 424/486 |
| 6,719,967 B1 | 4/2004 | Brown et al. | 424/70.1 |
| 6,797,742 B2 | 9/2004 | Kilgour et al. | 523/107 |
| 6,803,047 B1 | 10/2004 | Dupuis | 424/401 |
| 6,875,425 B2 | 4/2005 | Harichian et al. | 424/59 |
| 6,911,195 B2 | 6/2005 | Vu et al. | 424/65 |
| 7,208,480 B2 | 4/2007 | Williams et al. | 514/54 |
| 7,247,294 B1 | 7/2007 | Shore et al. | 424/62 |
| 7,250,158 B1 | 7/2007 | Shore et al. | 424/62 |
| 7,270,805 B1 | 9/2007 | Shore et al. | 424/62 |
| 7,288,616 B2 | 10/2007 | Tamareselvy et al. | 526/333 |
| 7,385,019 B2 | 6/2008 | Maroy et al. | 526/307.2 |
| 2001/0056049 A1 | 12/2001 | Aronson et al. | 510/130 |
| 2002/0015684 A1 | 2/2002 | Vatter | 424/70.12 |
| 2003/0049282 A1 | 3/2003 | Aronson et al. | 424/401 |
| 2004/0102562 A1 | 5/2004 | Butuc | 524/474 |
| 2004/0219215 A1 | 11/2004 | Bavouzet et al. | 424/486 |
| 2004/0241305 A1 | 12/2004 | Blindt et al. | 426/573 |
| 2005/0031568 A1 | 2/2005 | Deckner | 424/70.17 |
| 2005/0042192 A1 | 2/2005 | Evans et al. | 424/70.11 |
| 2005/0175570 A1 | 8/2005 | Inoue et al. | 424/70.15 |
| 2006/0088495 A1 | 4/2006 | Harichian et al. | 424/70.28 |
| 2006/0239947 A1 | 10/2006 | Dias et al. | 424/70.1 |
| 2007/0054820 A1 | 3/2007 | Harichian et al. | 510/130 |
| 2007/0161524 A1 | 7/2007 | Counradi et al. | 510/130 |
| 2007/0224133 A1 | 9/2007 | McGill | 424/49 |
| 2007/0244294 A1 | 10/2007 | Pavlin | 528/340 |
| 2008/0071077 A1 | 3/2008 | Dijk et al. | 536/56 |

FOREIGN PATENT DOCUMENTS

| | | |
|---|---|---|
| CA | 2091523 A1 | 10/1993 |
| DE | 127578 | 10/1977 |
| DE | 127578 | 10/1997 |
| EP | 355908 A1 | 2/1990 |
| EP | 0 432 835 | 12/1990 |
| EP | 1518533 | 3/2005 |
| EP | 1518533 A2 | 3/2005 |
| GB | 1372701 | 11/1974 |
| GB | 1450881 | 9/1976 |
| JP | 61-113601 | 5/1986 |
| JP | 61113601 | 5/1986 |
| JP | 03031389 | 2/1991 |
| JP | 2000144185 A | 5/2000 |
| JP | 2000159624 A | 6/2000 |
| JP | 2002-204951 | 7/2002 |
| JP | 2006182664 A | 7/2006 |
| JP | JP2008074706 A | 4/2008 |
| WO | WO0166600 A1 | 9/2001 |
| WO | 2007/089484 | 8/2007 |
| WO | 2007/109260 | 9/2007 |
| WO | WO2007109240 A2 | 9/2007 |
| WO | WO2007109282 A2 | 9/2007 |
| WO | 2008/081175 | 7/2008 |
| WO | WO2010009989 | 1/2010 |
| WO | WO2010097370 | 9/2010 |

OTHER PUBLICATIONS

Tadros et al., "*Personal care emulsions based on surfactant-biopolymer mixtures: correlation of rheological parameters with sensory attributes*" Colloids and Interface Science Series (2008), vol. 4, pp. 106-126.

(Continued)

*Primary Examiner* — Rebecca Prouty
*Assistant Examiner* — Danielle Sullivan
(74) *Attorney, Agent, or Firm* — Ronald A. Koatz

(57) ABSTRACT

The invention relates to process for making highly concentrated, spherical biopolymer gel particle suspensions comprising particles of defined particle diameter (e.g., range of 1 to 50µ) utilizing high internal phase emulsion as an intermediate.

15 Claims, No Drawings

(56) References Cited

OTHER PUBLICATIONS

PCT International Search Report in PCT application PCT/EP2011/065141 dated Dec. 15, 2011 with Written Opinion.

Abstract, Polyether-modified silicone elastomer used in personal care formulations, Research Disclosure—Abstract, May 10, 2000, 889, vol. 433 No. 5, Thomson Reuters, US.

Ayannides, A rheological study on microemulsion gels of isopropyl myristate, Polysorbate 80, Journal of Cosmetic Science, 1999, 1-7, vol. 50 No. 1, Society of Cosmetic Chemists, US.

Barry, The rheological properties of carbopol gels. I., International Journal of Pharmaceutics—Abstract, ., 1-25, vol. 2 No. 1, US, 1979.

Budtova, Shear-induced controlled release of aqueous solutions from micro-gels—Abstract, Macro 2004, International Conference on Polymers for Advance Technolgies, 2004, ., ., US.

Claro, Surface tension and rheology of aqueous dispersed systems containing a new hydrophobically, International Journal of Pharmaceutics—Abstract, ., 45-53, vol. 347 No. 1-2, Elsevier B.V., US, 2008.

Hjerten, The Preparation of Agarose Spheres for Chromatography of Molecules and Particles, Biochimica Biophysica Acta, 1964, 393-398, 79, US.

Kopolow, A new thickener/stabilizer technology, Cosmetic & Toiletries—Abstract, ., 61-7, vol. 108 No. 5, US, 2003.

Nishinari, Rheology and DSC of hydrocolloids, Foods & Food Ingredients Journal of Japan—Abstract, ., 4-16, vol. 212 No. 1, FFI Janaru, US, 2007.

Ryklin, Shear-thinning lamellar gel network emulsions as delivery systems, Delivery System Handbook for Personal Care and Cosmetic Products—Abstract, ., 547-568, ., US, 2005.

Tsai, Viscosity changes of APF gels under shearing effects, Journal of Pedodontics—Abstract, 1988, 281-93, vol. 12 No. 3, US.

Zhou et al., Preparation of uniform-sized agarose beads by microporous, Journal of Colloid and Interface Science, Feb. 11, 2007, 118-127, 311, Elsevier, US.

\* cited by examiner

HIPE-GELATION PROCESS FOR MAKING HIGHLY CONCENTRATED, SPHERICAL BIOPOLYMER GEL PARTICLE SUSPENSIONS

FIELD OF THE INVENTION

The present invention relates to novel suspensions comprising highly concentrated spherical biopolymer gel particles. The suspensions are prepared using a novel HIPE-Gelation process (the HIPE being an intermediate product prior to cooling to form the final suspensions) where water-in-oil high internal phase emulsions (HIPEs) comprising water soluble biopolymers (e.g. agarose) are formed at elevated temperatures and the HIPEs are subsequently cooled such that the water phase gels to form the novel, highly concentrated spherical biopolymer gel particle suspension. The HIPE intermediates are formed at elevated temperature from the combination of (1) an aqueous phase comprising biopolymer in polar or water solvent solution (optionally further comprising water soluble actives); and (2) nonionic surfactant in oil solutions. Through proper selection of surfactants/oils; biopolymer concentration (e.g., ratio of biopolymer to solvent); and mixing conditions, e.g., temperature and shear, it is possible to prepare a high concentration of spherical particles (in the suspension upon gellation) having the desired size range and excellent sensory characteristics. Moreover, the suspensions can be prepared on a commercial scale in a simple and efficient process where concentrated, spherical particles are preferably prepared without the need of a homogenizer operating under a pressure of up to 20,000 psi, or even up to 45,000 psi. The concentrated, spherical gel particle suspensions made according to this invention may be used "as is", or may be incorporated into an aqueous or oil based personal care product to deliver a unique sensory feel.

BACKGROUND OF THE INVENTION

High internal phase emulsions have been known for many years, and have found applications in areas such as food preparation, fuels, oil recovery and cosmetics. Typically, HIPEs are defined as a class of emulsions with a volume fraction of dispersed (internal) phase above 0.74. Examples include mayonnaise, an oil-in-water HIPE with greater than 75% oil droplets suspended in less than 25% external water phase; and Dove® smooth and soft anti-frizz cream, a water-in-oil HIPE with 80% water droplets suspended in less than 20% continuous silicone phase.

High internal phase emulsions are also widely used as a template to create highly porous materials. For example, the internal phase is water and the external oil phase consists of polymerizable monomers. Upon polymerization and removal of the internal water phase a highly porous cellular structure is created. This is widely referred to as PolyHIPE.

In the cosmetic and personal care industry, particles have been widely used in products to provide unique sensory attributes. Biopolymer particles (e.g., agarose, carrageenan) have gained considerable ground, due to their unique properties, as well as to their environmental friendliness or biodegradability.

In a co-pending application U.S. Ser. No. 12/392,646, entitled "Shear Gels and Compositions Comprising Shear Gel", filed Feb. 25, 2009, applicants disclose shear gel compositions which comprise biopolymer particles prepared in water or polar solvent. These shear gels are prepared by heating a biopolymer/solvent mixture and cooling, with shear, through the gellation temperature of the biopolymer. Particles produced upon cooling or gellation are irregular in shape (e.g., are not predominantly spherical), and have diameter varying from about 1 to 200 microns, preferably 8 to 50 microns. The shearing apparatus comprises a homogenizer operating under a pressure up to 20,000 psi (pounds per square inch), or even up to 45,000 psi.

S. Hjerter (Biochim. Biophys. Acta, 79 (1964) 393-398), discloses a method to prepare spherical agarose particles via suspension-gellation for application in Chromatography. Hot agarose solution is poured into an organic liquid containing hydrophobic stabilizer followed by cooling under agitation. The suspension formed is not a concentrated gel particle suspension and the final suspension contains less than 40% agarose gel. Further, toxic, organic solvents are used in preparation of the suspension and those solvents must be removed. More recently Q-Z Zhou et al (Journal of Colloid and Interface Science 311 (2007) 118-127) reported a preparation method of uniform-sized agarose beads prepared using a microporous membrane emulsification technique. This technique comprises pressing hot agarose solution through uniform-sized pores of the membrane into the oil phase.

Although both methods produced suspensions comprising spherical agarose beads, they have disadvantages in applications in personal care industry and production scale-up. S. Hjerter's method creates a suspension containing less than 40% agarose gel (e.g., is not concentrated as required by suspension of our product). Further, toxic organic solvents must be removed in order to be suitable in personal care industry; filtering/washing of beads increases the process complexity, generates waste and increases cost. Q-Z Zhou's method has issues in scale-up as processes involving microporous membranes generally do. Further, only dilute emulsions (i.e., these are not concentrated suspensions) were reported via the microporous membrane emulsification technique.

The present invention is directed to a process for making novel highly concentrated, spherical gel particle suspensions, wherein a high internal phase emulsion (HIPE) is used as a template or intermediate to create the final concentrated, spherical biopolymer gel particle suspension (i.e., by passing through an intermediate HIPE phase in processing, a novel suspension is formed upon gellation). The final suspension prepared may be used in aqueous or oil based personal care products, or alternatively, gel particle suspensions formed by the process of this invention can be used as is. Both the product formed and the process for forming the gel particle suspensions (HIPE-gelation process) are novel. The process comprises 1) dissolving biopolymer into water or polar solvent (and optional water soluble actives) at elevated temperature to form highly concentrated internal aqueous phase of the HIPE; 2) forming an external oil phase by mixing nonionic surfactant and oils; 3) gradually adding biopolymer solution into the oil phase under moderate agitation (e.g., high pressure homogenization is preferably avoided) to form the HIPE intermediate and 4) cooling the mixture to a temperature below the biopolymer gelation temperature, to form a suspension comprising the concentrated, spherical biopolymer particles of desired size and elasticity. Desired elasticity of particles in the suspension can be manipulated by varying biopolymer concentration used to form the aqueous phase forming the HIPE intermediate (e.g., using 0.01 to 15%, preferably 1 to 10% biopolymer as starting material relative to the aqueous phase). Desired size of particles can be manipulated by choice of oil and or surfactant and or shear through cooling. By this process a suspension can be produced, upon cooling, whereby sensory gel particles can make up 60 to 99% by wt. of the final suspension product. The level of surfactant (having HLB <15, preferably <10, more preferably <7) used in preparation of the HIPE intermediate can be as low as 0.01% by wt. The process may be readily carried out in a general purpose mixer known to those skilled in the art. The particle suspension prepared in this way may be incorporated into an aqueous or oil based personal care product without any destabilizing effects.

The above described process is referred to as HIPE-Gelation process. The process does not require the use of (and preferably avoids use of) high shear devices (e.g. Silverson Rotor-Stator mixer) or high pressure homogenizer, resulting in significant energy saving and savings in capital investment. Furthermore, because the final gel suspension may contain less than 10% by volume nonionic surfactant and oils (used in formation of the HIPE prior to cooling to form the suspension), a high yield of sensory particles (concentrated suspension) is produced. Furthermore, the nonionic surfactant and oils used in forming the HIPE intermediate may be chosen from a range of widely used surfactants and oils in the personal care industry. The suspensions formed from the process are themselves novel in that they comprise highly concentrated, spherical; gel particles suspensions (with some nonionic surfactant and some oil into which particles are suspended). Any composition comprising the novel suspensions prepared by said novel process are, of course, themselves novel.

SUMMARY OF THE INVENTION

More specifically, the present invention is directed to a HIPE-gellation process (where the HIPE is intermediate product prior to cooling to form the gel suspension) for making highly concentrated, spherical, biopolymer gel particle suspensions comprising:

1) 60 to 99 wt %, preferably greater than 74 to 95 wt % of the final suspension spherical, biopolymer gel particles (before cooling HIPE intermediate) (the biopolymer suspension product is claimed as a separate co-pending application); wherein a water or polar solvent solution comprising biopolymer (existing as the internal aqueous phase of the HIPE) is combined with the external oil phase to form the HIPE and is cooled to form the suspension. The ratio of biopolymer to water or polar solvent in forming the aqueous phase of the HIPE is 0.01/99.9 to 15/85 by wt, preferably 2/98 to 5/95 by wt. The biopolymer gel particles are spherical upon production of the suspension; and the average diameter of the particles in the suspension is 1-50μ, preferably 5 to 40μ; and 2) 1 to 40% by wt., preferably 1 to 20%, more preferably 1 to 10% by wt. of the final suspension of oils and surfactants used in the formation of HIPE intermediate which in turn is used to form the suspension and which are found in the HIPE (as well as in the final suspension) in the following amounts:

(a) 0.1 to 30 wt %, preferably 1 to 9 wt % of the HIPE intermediate of an oil or oil mixture which functions as the suspending medium for the above mentioned biopolymer particles in (1) upon formation of the suspension;

(b) 0.01 to 10 wt %, preferably 0.1 to 2% wt. of HIPE intermediate of a surfactant or surfactants which are dissolved or dispersed in the above mentioned oil or oil mixture in a)

wherein said surfactant preferably comprises a nonionic surfactant and has a hydrophilic-lipophilic balance (HLB) less than 15, preferably less than 10, more preferably less than 7;

The size of the spherical gel particles, and viscosity of the suspensions formed upon gellation are affected by the particular biopolymer molecule used; the concentration of the biopolymer relative to the total amount of water (e.g., 0.01-15% biopolymer as starting material when forming the internal aqueous phase); the particular surfactant and oil used; and the temperature at which the HIPE intermediate is formed. These conditions can thus be used to control the physical properties (size and hardness of particles) of the biopolymer gel particles in the final suspension which in turn will impact the sensory properties delivered from these particles when used "as is" or when added to a product.

Specifically, the suspensions are prepared by a HIPE-gelation process (subject of this application) used to prepare the highly concentrated spherical, biopolymer gel particle suspensions as noted above. This process comprises:

(a) forming an aqueous phase solution by dissolving 0.01 to 15% by wt., preferably, 1 to 10% by wt. biopolymer into water and/or polar solvent, as well as optional water-soluble active (ratio of biopolymer to water and/or polar solvent is 0.01/99.99 to 15/85 by wt.), in a properly sized vessel; and heating dispersion formed to a temperature, typically 60° to 100° C., preferably 70° to 90° C., which is above the gellation temperature of the biopolymer to produce a homogeneous mixture deplete of non-swollen biopolymer particulate (e.g., all biopolymer is dissolved in the aqueous phase);

(b) dissolving or dispersing a surfactant or surfactants into an oil or oil mixture in a separate and properly sized vessel, and heating the said solution or dispersion to a temperature above the gellation temperature of the gellation temperature of the biopolymer, typically 60 to 100° C., preferably 70° to 90° C.;

wherein said surfactant comprises nonionic surfactant having an HLB less than 15, preferably less than 10, more preferably less than 7;

(c) dispersing biopolymer solution of (a) into the said oil solution or dispersion of (b) preferably with agitation at a temperature, typically 60° to 100° C., preferably 70° to 90° C., which is above the gellation temperature of the biopolymer wherein said biopolymer solution is dispersed into the oil mixture containing (1) surfactant (0.01 to 10% preferably 0.1 to 2% wt. of the overall HIPE intermediate formulation; this is the same amount that will be found in final suspension upon cooling); and (2) oils (0.1 to 30%, preferably 1 to 9% by wt of the overall HIPE intermediate formulation; same amount that will be found in suspension upon cooling) at a temperature (preferably 70° to 90° C.) which is above the gelation temperature of the biopolymer, all done with moderate agitation; a water-in-oil high internal phase emulsion (HIPE) is formed with the aqueous biopolymer phase as internal aqueous phase, in the form of small spherical droplets of 1 to 50 microns suspended in oils which is the continuous phase (this is the HIPE intermediate product);
and (d) cooling (gellation step in the HIPE gellation process) said HIPE containing biopolymer solution as internal aqueous phase; the viscosity of biopolymer solution within the said small spherical droplets of 1 to 50 microns increases as a result of hydrogen bonding between biopolymer molecules. When cooling to below biopolymer gellation temperature, typically 25° to 50° C., preferably 30° to 40° C., the biopolymer solution droplets gel to form gel particles, wherein said gel particles have size ranging from 1-50µ in diameter and wherein the particles are spherical The aqueous biopolymer phase (e.g., biopolymer in water or in polar solvent) may be as high as 99% by weight (60 to 99% by wt.) of the final suspension after gellation (same concentration as is found in intermediate HIPE before gellation); and surfactants and oil may together be 40% or less by wt. of the suspension. Preferably, oil phase wt. % in suspension is 20% or less, more preferably 1-10%. As noted, gel particles will form at the gellation temperature of the biopolymer. For example, when agarose is used, the water droplets harden to gel particles at temperatures less than 35-40° C.

The size of the gel particles, and viscosity of the final suspensions are affected by the particular biopolymer molecule used; concentration of the biopolymer (e.g., 0.01 to 15% biopolymer dissolved into water and/or polar solvent); the particular surfactant and oil used; and the temperature at which the HIPE is formed. These conditions can thus be used to control the physical properties (size and hardness of particles) of the biopolymer gel particles which in turn will impact the sensory properties delivered from these particles.

In another embodiment, the subject invention relates to a method to control sensory properties of biopolymer gels by controlling the size and hardness of gel particle suspensions formed. Desired size and texture of gel particles can be achieved by proper choice of (a) biopolymer; (b) concentration of biopolymer (0.01-15%, preferably 1-10% biopolymer in water and/or polar solvent plus optional water soluble colorants and skin beneficial actives); (c) surfactant type and concentration; and (d) type of oil.

Because the gel particle suspensions formed can be used as final product (e.g., to sell directly) or can be further integrated into a base to form final creams or multiple emulsions, for example, the manipulation of the gel particle suspension's physical property can be used to control sensory properties of the final product in which it is incorporated. Thus, the biopolymer concentration, choice of oils and/or surfactants, and the temperature at which the HIPE is formed may also be used to manipulate sensory properties of the final product.

In another embodiment, the invention may comprise topical compositions containing the gel particle suspension made by the process of the invention.

Finally, it should be noted that the gel particle suspensions may also be used to encapsulate water soluble actives (e.g., glycerine or hydroxypropyltri($C_1$ to $C_3$ alkyl) ammonium salts may be encapsulated within the gel particle) which actives can be released from the gel particles as moisturizing agents. The active can be incorporated when the particle suspensions are sold as produced; or, as noted above, the gel particle suspensions (with active encapsulated in the gel particles) may be introduced into topical composition, one of the embodiments of the invention.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental example, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y" it is understood that all ranges combining the different endpoints are also contemplated; and "x to y" are understood to subsume all values in this range. Where the term "comprising" is used in the specification or clams, it is not intended to exclude any terms, steps or features not specifically recited. All temperatures are in degrees Celsius (° C.) unless specific otherwise. All measurements are in SI units unless specified otherwise. All documents cited are—in relevant part—incorporated herein by reference.

DETAILED DESCRIPTION OF THE INVENTION

The present invention relates to a process for making novel highly concentrated (60 to 99% of final suspension), spherical biopolymer gel particle suspensions. The gel particles comprise a high volume fraction of the suspension. The particles are formed by a combination of biopolymer and water or polar solvent which are formed initially in a heated solution (as aqueous internal phase) before combining with separate oil/surfactant phase to form a HIPE intermediate and subsequently cooling to form gel suspension. It should be noted the biopolymer may also be encapsulating water soluble actives.

Unexpectedly, applicants have found that, with proper selection of biopolymers (e.g., type and/or concentration), surfactants and oil; and with proper processing conditions, it is possible to produce these highly concentrated, spherical biopolymer gel particle suspensions (suspensions are claimed in separate application). The suspensions are made through a water-in-oil high internal phase emulsion (HIPE)-gellation process, subject of the present application. The suspensions comprise highly concentrated, biopolymer gel particles which are spherical and with distribution of gel particles range from 1-50µ in diameter. In terms of shape, the uniformity of the gel, and ease of processing, the suspension differs from shear gels and processes of previous work applicant have done in recent filings (U.S. Ser. No. 12/392,646, entitled "Shear Gels and Compositions Comprising Shear Gel", filed Feb. 25, 2009). The biopolymer gels of '646 are irregular in shape, compared to spherical shape of particles of the invention. Additionally, the polymer gels are not uniform and have polymer rich and polymer poor regions. The biopolymer gels of comparable particle size of '646 were made without utilizing the principle of emulsification as is used in this invention. Further, particles of '646 were obtained with high pressure homogenizing, while the HIPE-gellation process of our invention obtains concentrated, spherical particles even without such high pressure homogenization and associated use of high shear devices.

Thus, suspensions made by process of the present invention comprise highly concentrated spherical gel particle suspension (produced upon cooling of a heated HIPE solution) comprising:

1) 60% to 99% by wt., preferably >74% to 95% by wt. of final suspension of spherical biopolymer gel particles; and
2) 1-40%, preferably 1-20%, more preferably 1-10% by wt. of the final suspension of oils and surfactants wherein amounts of oils and surfactants used in the formation of the HIPE (prior to cooling to form the suspension) is:
   (a) 0.1 to 30%, preferably 1 to 9% by wt. of an oil or oil blends; and
   (b) 0.01 to 10% by wt., preferably 0.1 to 2% by wt. of a nonionic surfactant or surfactants blends.

The HIPE is typically prepared by gradually dispersing an internal hot aqueous phase comprising biopolymer dispersed into water and/or polar solvent (and optional water soluble active) into a hot external phase comprising surfactants(s) dispersed into an oil or oil mixture. Dispersion of the internal phase into the external phase is done with moderate agitation in a general purpose mixer known to those skilled in the art (but preferably not under high pressure homogenization). Upon cooling to below the gellation temperature of the biopolymer, droplets of the HIPE composition harden into a suspension comprising gel particles. The gel particles are of diameter 1 to 50, preferably 5 to 40 microns.

In another embodiment, the elasticity/hardness and the size of the biopolymer gel suspension can be controlled by controlling concentration of starting biopolymer (during formation of the aqueous phase) as well as choice of surfactant and oil (used during formation of the oil phase). In other words, these parameters can be used to control sensory properties of the concentrated, spherical biopolymer gel particle suspension formed when the intermediate high temperature HIPE product is cooled; or to control sensory properties of the topical compositions in which particle suspension is used.

Biopolymer suitable for use in this invention may be chosen from the group consisting of polysaccharides, proteins and mixtures thereof such as those disclosed in co-pending U.S. application Ser. No. 12/392,646.

The biopolymer used as starting reagents are macromolecules suitable for swelling with water, polar solvent or both and may be synthetically made, but are normally produced by living organisms. Those pure biopolymer can be, for example, grain-like, powdery, and crystalline or the like.

Preferably, the biopolymer can be chosen, for example, from carrageenan, furcellaran, pectin, alginate, agar, agarose, gellan, glucomannan (e.g., Konjac), galactomannan (e.g., locust bean gum, guar), xanthan, modified cellulose, glucan (e.g., starches, curdlan), gelatin, whey protein or mixtures thereof. More preferably, the biopolymer used is agar, agarose, carrageenan, or a mixture thereof. In a most preferred embodiment, the biopolymer used is agarose.

The biopolymers suitable for use in this invention are made commercially available from suppliers like FMC Corporation; National Starch and Chemical Co.; Cyber Colloids Ltd., as well as Hispangar, S.A. Additional descriptions of the types of biopolymers that may be used in this invention may be found in Food Gels, Chapter 1, edited by Peter Harris, Elsevier, 1990 and U.S. Pat. Nos. 6,673,371 and 5,738,897, the disclosures of which are incorporated herein by reference.

The biopolymer can optionally be used in combination with a synthetic thickener. Illustrative thickeners which may be suitably used include alkylated polyvinylpyrrolidones like butylated polyvinyl pyrrolidone sold under the name Ganex® line by ISP Corporation, terephthalate polyesters like polypropylene terephthalate and ammonium acryloyldimethyltaurate/VP Copolymer, both sold under Aristoflex® line by Clariant A.G.; and mono alkyl esters of poly(methyl vinyl/ether maleic acid) sodium salt, like that included in the EZ Sperse® line made available by ISP Corporation, as well as (3-dimethylaminopropyl)-methacrylamide/3-methacryloylamidopropyl)-lauryl-dimethyl-ammonium chloride like that included in the Styleze® line made available by ISP Corporation. Other thickeners suitable for use include those generally classified as acrylic acid/ethyl acrylate copolymers and carboxyvinyl polymers made available by the B.F. Goodrich Company under the Carbopol name. Such thickeners consist essentially of colloidally water-soluble poly-alkenyl polyether cross-linked polymer of acrylic acid crosslinked with a crosslinking agent like polyallyl sucrose or polyallyl pentaerythritol. These thickeners include, for example, Carbopol 934, 940, 950, 951, 980 and 981.

Other examples of suitable synthetic thickeners for use herein include those sold under the name Carbopol Ultrez 10, Carbopol Ultrez 21, Carbopol ETD2020, Carbopol 1342, Carbopol 1382, and Pemulen TR-1 (CTFA designation: Acrylates/10-30 Alkyl Acrylate Cross-polymer). Still other examples of suitable thickeners include those made available by Seppic under the names Sepigel 305 and Sepiplus. If desired, combinations of synthetic thickeners may be employed whereby those classified as acrylate-derived and/or terephthalate polyesters are generally preferred.

Typically, the concentration of the biopolymer relative to the amount of water or polar solvents in the formulation is about 0.01 to about 15%, preferably 0.1 to about 10%, most preferably about 0.2 to about 7% by wt. biopolymer including all ranges subsumed therein. When synthetic polymer is desired, the same typically makes up from about 0.001 to about 6%, and preferably, from about 0.01 to about 4.0%, and most preferably, from about 0.015 to about 2.5% by weight synthetic polymer and including all ranges subsumed therein.

The exact concentration of biopolymer is important for controlling the elasticity (hardness) of the biopolymer gel finally formed when HIPE (in turn formed from combination of aqueous biopolymer phase and surfactant/oil solution) is cooled. That is by increasing the levels from less than 0.1% biopolymer to levels as high as 10-15% (relative to water/polar solvent) we can form biopolymer gel particles in the gel particle suspension which range in elasticity from less $10^2$ Pa to greater than $10^4$ Pa.

The solvent with which the biopolymer is combined may be water or a polar, hydrophilic solvent. Illustrative yet nonlimiting examples of the type of polar solvent that may be used (with or without water) in this invention are sorbitol, hydroxypropyl sorbitol, glycerine, ethoxylated glycerol, propolylated glycerol, polyalkylene glycols like polyethylene glycol and polypropylene glycol, diethylene glycol, dipropylene glycol, triethylene glycol, 2-ethoxyethanol, hexylene glycol, butylene glycol, hexamatriol, mixtures thereof or the like.

It should be noted that the gel particles in the suspension can also be used to encapsulate water soluble colorants and skin benefit actives such as those selected from the group consisting of glycolic acid, amino acids, glycerine, hydroxypropyl tri($C_1$ to $C_3$ alkyl) ammonium salts or mixtures thereof. When released from the particles for use (either if particle suspension is sold as stand alone product, or incorporated into topical compositions), the particles can be used as moisturizers or other appropriate function.

As indicated, the solvent and biopolymer and optionally other thickeners, emollients to be included in the biopolymer particle gel are combined at elevated temperature (i.e., at temperature above gellation temperature of biopolymer), and dispersed into the oil phase to form the HIPE, and are cooled with moderate agitation using standard mixing equipment known to those skilled in the art to form gel particle suspension.

When cooled below the gellation temperature, the biopolymer gel particles formed comprise 60 to 99%, preferably >74 to 99, more preferably 80 to 95% by weight of the final gel particle suspension.

The surfactants used in formation of the HIPE (i.e., when biopolymer solution is combined with surfactant/oil solution) are preferably low HLB nonionic emulsifiers but could contain low levels of other type of surfactants such as anionic, amphoteric, zwitterionic, cationic or mixtures thereof.

Preferably, the surfactant is a nonionic surfactant having a hydrophilic-lipophilic balance (HLB) of less than 15, preferably 10 or less, more preferably 7 or less. Typical example of such low HLB surfactants include linear or branched or cross-linked dimethicone polymers modified with polyether and/or alkyl chain (e.g., Shin Etsu KF series with HLB<7, KSG 200 series, KSG 300 series, KSG 700 series, KSG 800 series, Abil em 90, 97); esters of sorbitan with fatty acids (e.g. Span20-80 series); cremophor A6 (ceteareth-6 and steary alcohol), A25 (ceteareth-25) and GS 32(polyglyceryl-3 distearate) from BASF, sucrose esters (e.g. Sucrose stearate S-170, -270, -370 -570 from Mitsubishi-Kagaku Foods Corporation), monoglyceride based surfactants.

Particularly, preferred surfactants include polyether modified cross-linked silicone polymers (e.g., PEG-15/lauryl dimethicone cross-polymer such as KSG-310® from Shin Etsu); polyalkylene glycol derivatives of dimethicone (e.g., cetyl polyethylene glycol/polypropylene glycol-10/1 dimethicone, such as Abil EM90®; PEG-10 dimethicone, such as KF®-6017 from Shin-Etsu or lauryl PEG-9 polydimethylsiloxyethyl dimethicone, such as KF®-6038 from Shin-Etsu); esters of sorbitan (e.g., sorbitan monooleate, such as Span® 80 from Croda); and mixtures thereof.

Typically, surfactant comprises 0.01 to 10%, preferably 0.05 to 3%, more preferably 0.1-2% by wt. of the HIPE composition (referred to as suspension upon cooling) including all ranges subsumed therein.

The surfactant(s) are typically dissolved or dispersed in oil or oil blends. A wide range of oils can be used, including mineral oil, organic oil or silicone oils. Finally, oils which are widely used in the cosmetic industry may be used.

Preferably, the oil is selected from the group consisting of mineral oils (e.g., Pionier® 6501, Lilac® 100); silicone oils (e.g., DC200/50 cts. from Dow Corning); triglyceride oils (e.g., caprylic/capryl triglycerides); $C_8$-$C_{24}$ chain length ester derivatives of $C_1$-$C_{10}$ carbons (e.g., isopropyl myristate); and mixtures thereof.

The oil or oil mixture (which function as suspending medium for the biopolymer particles) comprise 0.1 to 30%, preferably 1 to 9% by wt. of the HIPE intermediate before the HIPE is cooled to form the suspension. These are the same percentages of oil or oil mixture in the suspension when cooled.

It has been noted that certain specific combinations of oil and surfactant should be avoided in order to prepare stable HIPE. These include combination of Abil EM90® and silicone oil wherein silicone oil is the only other oil present in the oil phase; or combination of Abil EM90® and light mineral oil (e.g., lilac 100). Surprisingly, Abil EM90® functions well when mineral oil and silicone are combined together; or when heavier mineral oils are used.

Together the surfactant(s) and oil comprise the external phase of the HIPE (particle gel suspension upon cooling) and may comprise 1 to 40%, preferably 1 to 10% by weight of both the HIPE and the final suspension (upon cooling).

Upon cooling of the HIPE, the gelled biopolymer solution in the internal phase will comprise particles which are spherical in shape and the particles will have a diameter of between 1-50 μm, preferably 5-40 μm, more preferably 10-25 μm.

In another aspect of the invention, the invention comprises a HIPE gellation process (claimed in a separate application) for making the novel gel particle suspension of the subject invention.

The process of this aspect of the invention involves forming a solution of biopolymer as defined above and water and/or polar solvent, preferably with mixing wherein the biopolymer-solvent mixture is heated to a temperature above the gellation temperature of the biopolymer and preferably to a temperature that is above the gellation temperature of the resulting biopolymer. Preferably, the mixture is heated to a temperature from about 60° C. to about 100° C., and most preferably, to a temperature from about 70° C. to about 90° C., including all ranges subsumed therein. Heating occurs until a homogeneous mixture is prepared. Separately, a solution of surfactant or surfactants and oil, both as described above, is prepared and the biopolymer solution and surfactant solution are then combined to form a HIPE using standard mixing equipment (e.g., preferably, with no high pressure homogenization).

The HIPE solution is then cooled through the gellation temperature of the biopolymer to form the concentrated spherical gel particle suspension of the subject invention. The HIPE may be stirred while cooling using standard mixing equipment.

It is a key aspect of the invention, as noted, that the gel suspension may be formed while avoiding high-pressure homogenization; and while obtaining high concentration of biopolymer gel particles (e.g., from the internal phase of the HIPE) which are in a spherical shape and have a size ranging from 1-50 μm.

In another aspect of the invention, the invention comprises a method of manipulating the hardness of the biopolymer gel particles in the gel particle suspension and, therefore, influencing sensory properties.

This can be done in a number of ways which include (1) selection of surfactant and/or oil into which biopolymer solution will be dispersed when forming the HIPE (prior to gellation); (2) controlling concentration of biopolymer itself in the biopolymer/solvent solution and (3) control of agitation rate during HIPE formation (again when biopolymer solution and oil/surfactant solution are combined). Specifically, this can control the hardness and size of the spherical particles (upon cooling of HIPE) in a way which allows applicants to modulate exactly what sensory feeling they wish to provide (based, for example, on evaluation of consumer sensory panels).

It is noted that the resulting highly concentrated, spherical, gel particle suspensions can be used or sold as final products with sensory profiles as determined by controlling the factors noted; or they can be made and sold as intermediate products to be used in topical compositions. The properties of the intermediate products can of course also be controlled depending on what effect is desired to be imparted on this final composition.

In another aspect of the invention, the invention relates to the use of the gel particle suspension in topical compositions.

Topical compositions of the present invention can, for example, be in the form of foam, liquid, lotion, cream, serum, gel, soap bar, cleansing product (e.g., body wash, facial wash or shampoo and conditioner) or toner, or applied via a face mask or patch. The topical composition of this invention is, preferably, a leave-on composition. Skin to which topical compositions are applied is meant to include skin on the face, neck, chest, back, arms, hands, buttocks, legs and scalp.

If used as part of a topical composition, the gel particle suspensions of the present invention can make up from about 1 to about 99%, and preferably, from about 3 to about 85%, and most preferably, from about 8 to about 60% by weight of the topical composition, based on total weight of the topical composition and including all ranges subsumed therein.

It should be known, however, that commercially acceptable and conventional vehicles may be used, acting as diluents and/or dispersants for the topical compositions of this invention, along with the gel particle suspensions (GPS).

Therefore, the cosmetically acceptable vehicle suitable for use in this invention may be aqueous-based, anhydrous, oil-based or an emulsion, including a multiple emulsion. If the use of water is desired, water typically makes up the balance of the topical composition. Silicone elastomers are typically not preferred in this invention since the biopolymers found in the GPS described herein are, surprisingly, excellent silicone elastomer mimetics. Optionally, however, silicone elastomers may be used along with the GPS.

In addition to water, organic solvents may be optionally included to act as carriers along with the GPS within the topical compositions of the present invention. Illustrative and non-limiting examples of the types of organic solvents suitable for use in the present invention include alkanols like ethyl and isopropyl alcohol, mixtures thereof or the like.

Other optional additives suitable for use along with the HIPEs of this invention include ester oils like isopropyl myristate, cetyl myristate, 2-octyldodecyl myristate, avocado oil, almond oil, olive oil, sunflower seed oil, neopentylglycol dicaprate, mixtures thereof or the like. Typically, such ester oils are used at an amount to yield a stable, and most preferably, water-in-oil emulsion when such an emulsion is desired. Other oils suitable for use include those generally classified as hydrocarbons, including those known as waxes.

Emollients may also be used, if desired, within the topical composition of the present invention. Alcohols like 1-hexadecanol (i.e., cetyl alcohol) are often desired as are the emollients generally classified as silicone oils and synthetic esters. Silicone oils suitable for use include cyclic or linear polydimethylsiloxanes containing from 3 to 9, preferably from 4 to 5, silicon atoms. Nonvolatile silicone oils useful as an emollient material in the inventive topical composition described herein include polyalkyl siloxanes, polyalkylaryl siloxanes and polyether siloxane copolymers. The essentially non-volatile polyalkyl siloxanes useful herein include, for example, polydimethylsiloxanes.

The ester emollients that may optionally be used are:
(1) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
(2) Ether-esters such as fatty acid esters of ethoxylated fatty alcohols.
(3) Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
(4) Wax esters such as beeswax, spermaceti, stearyl stearate and arachidyl behenate.
(5) Sterol esters, of which cholesterol fatty acid esters are examples.

Emollients, when used, typically make up from about 0.1 to about 50% by weight of the topical composition, including all ranges subsumed therein.

Fatty acids having from 10 to 30 carbon atoms may also be included within the composition of the present invention. Illustrative examples of such fatty acids include pelargonic, lauric, myristic, palmitic, stearic, isostearic, oleic, linoleic, arachidic, behenic or erucic acid, and mixtures thereof. Compounds that are believed to enhance skin penetration, like dimethyl sulfoxide, may also be used.

The polar solvents described herein may also be added as humectants in the desired topical composition of this invention. Therefore, such polar solvents may be used to make GPS, only as a humectant as an additive to the topical composition, or both. In an especially preferred embodiment, the topical composition of this invention has less than about 50% by weight polar solvent, and preferably, from about 0.001 to about 25% by weight polar solvent based on total weight of the topical composition and including all ranges subsumed therein.

Collectively, water, biopolymer gels, silicones, esters, fatty acids and/or humectants will be present in amounts from 1 to 99.9%, preferably from 80 to 99% by weight.

Surfactants may also be present in the topical compositions of the present invention. Total concentration of the surfactant will range from about 0 to about 40%, and preferably, from about 0 to about 20%, optimally from about 0.001 to about 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; mono- and di-fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, acyl glutamates, $C_8$-$C_{20}$ alkyl ether phosphates and combinations thereof. In an especially preferred embodiment, the surfactant employed is nonionic, and especially, polyoxyethylene sorbitan monopalmitate sold as Tween 40 by ICI Americas, Inc.

Perfumes may be used in the topical composition of this invention. Illustrative non-limiting examples of the types of perfumes that may be used include those comprising terpenes and terpene derivatives like those described in Bauer, K., et al., *Common Fragrance and Flavor Materials*, VCH Publishers (1990).

Illustrative yet non-limiting examples of the types of fragrances that may be used in this invention include myrcene, dihydromyrenol, citral, tagetone, cis-geranic acid, citronellic acid, mixtures thereof or the like.

Preferably, the amount of fragrance employed in the topical composition of this invention is in the range from about 0.0% to about 10%, more preferably, about 0.00001% to about 5 wt %, most preferably, about 0.0001% to about 2%.

Various types of optional ingredients/additives may be used in the topical compositions of the present invention. Although not limited to this category, general examples include talcs and silicas, as well as alpha-hydroxy acids, beta-hydroxy acids, zinc salts, and sunscreens.

Beta-hydroxy acids include salicylic acid, for example. Zinc pyrithione is an example of the zinc salts useful in the topical composition of the present invention.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation. Additives that reflect or scatter the suns rays may also be employed. These additives include oxides like zinc oxide and titanium dioxide.

Many topical compositions, especially those containing water, should be protected against the growth of potentially harmful microorganisms. Anti-microbial compounds, such as triclosan, and preservatives are, therefore, typically necessary. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, phenoxyethanol and benzyl alcohol. Preservatives will usually be employed in amounts ranging from about 0.1% to 2% by weight of the topical composition.

Still other optional ingredients/additives that may be used in the topical composition of this invention include chelators like EDTA, pH modifiers (e.g., NaOH), dioic acids (e.g., malonic acid, sebacic acid), antioxidants like vitamin E, retinoids, including retinoic acid, retinal, retinol and retinyl esters, conjugated linoleic acid, petroselinic acid and mixtures thereof, as well as any other conventional ingredients well known for wrinkle-reducing, anti-acne effects and reducing the impact of sebum.

Even other optional additives that may be employed in the topical composition of the present invention are skin lightening additives. Illustrative yet non-limiting examples of skin lightening additives that may be used in this invention are niacinamide, vitamin C and its derivatives, 12-hydroxystearic acid, resorcinols and their derivatives (including those esterified with, for example, ferulic acid, vanillic acid or the like), extracts of kudzu, chamomile, and yarrow as well as any mixtures of the skin lightening sources.

Often preferred optional additives suitable for use in the topical composition of this invention include sensory modifying particles like microcrystalline cellulose, silica modified ethylene/methacrylate copolymer microspheres, talc modified ethylene/methacrylate copolymer microspheres, mixtures thereof or the like. Other examples of the types of particles suitable for use in this invention include those comprising polyolefins like polyethylene, polypropylene and/or polybutylene-based polymers, polyamides (like nylon fibers), mixtures thereof or the like. Still other preferred particles suitable for use in this invention include those comprising polyurethane, polystyrene, epoxy resins, urea resins, silicone resins, mixtures thereof or the like.

In a preferred embodiment, the particles used in this invention comprise polyethylenes, or are talc comprising particles or mixtures thereof. The former are often sold under the names Cerapure (made commercially available by Shamrock), Asensa (made commercially available by Honeywell) and Miperon (made commercially available by Mitsui Petrochemical Industries, Ltd.). Another preferred polyethylene-based particle is sold under the name CL-2080 (made commercially available by Kobo Industries). Other preferred particles suitable for use in this invention include nylons (e.g., nylon-12) sold under the name SP-10 which is made commercially available by Kobo Industries. Still other preferred particles suitable for use in this invention include those comprising copolymers of ethylene and methacrylate that contain silica or talc and sold under the names SPCAT-12 and DSPCS-12, respectively, both of which are also made commercially available by Kobo Industries. Other particles comprising polystyrenes and polymethyl methacrylate (sold, for example, under the names Ganzpearl GS-0605 and GME0380, respectively) and made available from Presperse are also often preferred.

Even other particles suitable for use in this invention include natural polymeric spheroids like those which comprise starch and those which comprise silk, the former, for example, made available from National Starch and Chemical and the latter, for example, made available by Engelhard Corporation. Still other natural polymeric particles suitable for use in this invention include those natural polymeric particles comprising cellulose such as Celluflow and Cellulo Beads, the former made commercially available by Chisso Corporation and the latter made available by Kobo Industries.

When used, such particles typically make up from about 0.001 to about 10%, and preferably, from about 0.01 to about 8%, and most preferably, from about 0.1 to about 6% by weight of the total weight of the topical composition, including all ranges subsumed therein.

Other preferred optional additives suitable for use with the HIPEs of this invention include moisturizing agents like hydroxypropyl tri($C_1$-$C_3$ alkyl)ammonium salts. These salts may be obtained in a variety of synthetic procedures, most particularly by hydrolysis of chlorohydroxypropyl tri($C_1$-$C_3$ alkyl)ammonium salts. A most preferred species is 1,2-dihydroxypropyltrimonium chloride, wherein the $C_1$-$C_3$ alkyl is a methyl group. Amounts of the salt may range from about 0.2 to about 30%, and preferably from about 0.5 to about 20%, optimally from about 1% to about 12% by weight of the topical composition, including all ranges subsumed therein.

Ordinarily the $C_1$-$C_3$ alkyl constituent on the quaternized ammonium group will be methyl, ethyl, n-propyl, isopropyl or hydroxyethyl and mixtures thereof. Particularly preferred is a trimethyl ammonium group known through INCI nomenclature as a "trimonium" group. Any anion can be used in the quat salt. The anion may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate.

Still other preferred moisturizing agents which may be used, especially in conjunction with the aforementioned ammonium salts include substituted urea like hydroxymethyl urea, hydroxyethyl urea, hydroxypropyl urea; bis(hydroxymethyl)urea; bis(hydroxyethyl)urea; bis(hydroxypropyl)urea; N,N'-dihydroxymethyl urea; N,N'-di-hydroxyethyl urea; N,N'-di-hydroxypropyl urea; N,N,N'-tri-hydroxyethyl urea; tetra(hydroxymethyl)urea; tetra(hydroxyethyl)urea; tetra(hydroxypropyl urea; N-methyl, N'-hydroxyethyl urea; N-ethyl-N'-hydroxyethyl urea; N-hydroxypropyl-N'-hydroxyethyl urea and N,N' dimethyl-N-hydroxyethyl urea. Where the term hydroypropyl appears, the meaning is generic for either 3-hydroxy-n-propyl, 2-hydroxy-n-propyl, 3-hydroxy-1-propyl or 2-hydroxy-1-propyl radicals. Most preferred is hydroxyethyl urea. The latter is available as a 50% aqueous liquid from the National Starch & Chemical Division of ICI under the trademark Hydrovance.

Amounts of substituted urea that may be used in the topical composition of this invention range from about 0.01 to about 20%, and preferably, from about 0.5 to about 15%, and most preferably, from about 2 to about 10% based on total weight of the composition and including all ranges subsumed therein.

When ammonium salt and substituted urea are used, in a most especially preferred embodiment at least from about 0.01 to about 25%, and preferably, from about 0.2 to about 20%, and most preferably, from about 1 to about 15% humectant, like glycerine, is used, based on total weight of the topical composition and including all ranges subsumed therein. In yet another especially preferred embodiment, the topical composition of this invention is substantially free of silicone elastomer.

The topical composition of the present invention is intended for use primarily as a product for topical application to human skin, especially and at least as a product that may moisturize the skin. Thus, the inventors have discovered that the described HIPEs unexpectedly can be used as an excellent base in a topical composition to deliver excellent sensory benefits (e.g., silkiness) when the topical composition is, for example, substantially free of silicone elastomer. Other benefits from using the topical composition of this invention may include skin lightening, decreasing the effect of sebum on the skin and skin wrinkle reducing. In an especially preferred embodiment, the topical composition of the present invention has a pH from about 4.5 to about 7.5, including all ranges subsumed therein. Moreover, the topical composition of the present invention typically has a viscosity from about 4,000 to about 30,000, and preferably, from about 8,000 to about 25,000, and most preferably, from about 12,000 to about 23,000 cps initially and after 24 hours at ambient temperature (measured with a Brookfield DV-1 Viscometer, with RV-S06 spindle, 25° C., 20 rpm).

When making the topical composition of the present invention, the desired GPS is generally added after other ingredients are mixed and at temperatures from about 20 to about 70° C. and under atmospheric pressure.

The packaging for the composition of this invention can be a patch, bottle, tube, roll-ball applicator, propellant driven aerosol device, squeeze container or lidded jar.

The examples which follow are provided to illustrate and facilitate an understanding of the invention. The examples are not intended to limit the scope of the claims.

EXAMPLES

Example 1

The ingredients as listed in Table 1 below were used to prepare a typical HIPE (prior to gelation to form gel particle suspension) of the invention:

TABLE 1

| Material/Ingredient | Initial Phase for Preparation | Weight % by wt. | (Grams) | |
|---|---|---|---|---|
| Mineral Oil (Pioner 6501) | A1 | 5.00 | 12.50 | Oil Phase |
| KSG-310 (mixture of PEG-15/lauryl dimethicone cross-polymer and mineral oil*) | A2 | 5.00 | 12.50 | |
| Agarose | B1 | 1.80 | 4.50 | Aqueous phase |
| Deionized water | B2 | 88.20 | 220.50 | |

*KSG-310 ® from Shin Etsu

Using components of Table 1 above, the HIPE emulsion was prepared and cooled to form GPS as follows:

KSG-310 of phase A2 was mixed with mineral oil of phase A1 using standard mixing equipment and the two were heated above 75° C. In a separate beaker, agarose and water were combined (phase B) and heated with agitation to 75° C. When both aqueous phase B and oil phase A were at 75° C., phase B (aqueous phase) was slowly added to oil phase (A) under agitation. The components were mixed for about 10 minutes and then cooled under agitation. The resulting mixture comprises 90% by wt. spherical agarose gel particles of below about 40 microns. It should be noted that no additional homogenization step was required and the particles are spherical.

Examples 2-17 as well as comparatives were prepared using the same procedure and the weight percentages of ingredients used are listed in the following table:

TABLE 2

| | Examples | | | | | | | | | |
|---|---|---|---|---|---|---|---|---|---|---|
| Materials | 2 | 3 | 4 | 5 | 6 | 7 | 8 | 9 | 10 | 11 |
| KSG-310 (PEG-15/Lauryl Dimethicone Cross Polymer & mineral oil) | 5 | 5 | 1 | | | | 1 | | | |
| Cetyl PEG/PPG-10/1 Dimethicone (Abil EM 90) | | | | 1.5 | 0.19 | 0.15 | | | 0.15 | 0.15 |
| Lauryl PEG-9 Polydimethylsiloxyethyl Dimethicone (KF6038) | | | | | | | | | | |
| PEG-10 Dimethicone (KF-6017) | | | | | | | | 0.15 | | |
| Sorbitan monooleate (Span 80) | | | | | | | | | | |
| Mineral oil (Pionier 6501) | 5 | 5 | 9 | 8.5 | 9.81 | 7.55 | | | | |
| Moneral oil (Lilac 100) | | | | | | | 9 | | 6.15 | 4.61 |
| Silicone oil (DC200/50cts) | | | | | | | | 7.55 | 1.39 | 2.93 |
| Caprylic/capryl Triglyceride | | | | | | | | | | |
| Isopropyl Myristate | | | | | | | | | | |
| Agarose | 2.7 | 3.6 | 2.7 | 1.8 | 1.8 | 1.85 | 1.8 | 1.85 | 1.85 | 2.77 |
| Methylparaben | | | | | | | | | | 0.2 |
| DI water | 87.3 | 86.4 | 87.3 | 88.2 | 88.2 | 90.45 | 88.2 | 90.45 | 90.45 | 89.34 |
| Water phase, wt % | 90 | 90 | 90 | 90 | 90 | 92.3 | 90 | 92.3 | 92.3 | 92.31 |

TABLE 2-continued

| Materials | Examples | | | | | | Comparatives | | |
|---|---|---|---|---|---|---|---|---|---|
| | 12 | 13 | 14 | 15 | 16 | 17 | A | B | C |
| KSG-310 (PEG-15/Lauryl Dimethicone Cross Polymer & mineral oil) | | | | | | | | | |
| Cetyl PEG/PPG-10/1 Dimethicone (Abil EM 90) | 0.15 | | | 0.5 | 0.5 | 0.5 | | 0.15 | 0.15 |
| Lauryl PEG-9 Polydimethylsiloxyethyl Dimethicone (KF6038) | | 0.15 | | | | | | | |
| PEG-10 Dimethicone (KF-6017) | | | | | | | | | |
| Sorbitan monooleate (Span 80) | | | 0.15 | | | | | | |
| Mineral oil (Pionier 6501) | 6.15 | 7.54 | | | | 9.5 | 10 | | |
| Moneral oil (Lilac 100) | | | 4.61 | | | | | 7.55 | |
| Silicone oil (DC200/50cts) | 1.39 | | 2.93 | | | | | | 7.55 |
| Caprylic/capryl Triglyceride | | | | 9.5 | | | | | |
| Isopropyl Myristate | | | | | 9.5 | | | | |
| Agarose | 1.85 | 1.85 | 2.77 | 1.8 | 1.8 | 9 | 2.7 | 1.85 | 1.85 |
| Methylparaben | 0.2 | | | | | | | | |
| DI water | 90.26 | 90.45 | 89.54 | 88.2 | 88.2 | 81 | 87.3 | 90.45 | 90.45 |
| Water phase, wt % | 92.31 | 92.3 | 92.31 | 90 | 90 | 90 | 90 | 92.3 | 92.3 |

Stable gel particle suspensions were formed with agarose gel particles of 1-50 microns for Examples 2-17. No stable GPS was formed in Comparatives A, B and C. Comparative A shows that surfactant is required to form GPS. Comparative B and C show certain combinations of surfactant and oils are not suitable in forming GPS with a high internal phase (up to 92.3% by wt) and at very low surfactant level (as low as 0.15%). More specifically, Abil em 90, which contains alkyl branches, tends to stabilize GPS with mineral oils as external phase more than silicone oils, which explains why Comparative B fails to form GPS. In addition, due to the specific structure of Abil em 90, it tends to stabilize GPS with heavier mineral oils (such as Pionier 6501) as external phase more than lighter ones (Lilac 100) as shown in comparative C. Unexpectedly Abil em 90 can stabilize GPS with blends of silicone oil and lighter mineral oil from a ratio ranging 10:1 to 1:10. This can be explained by the fact that, in the oil blend, the lighter mineral oil imparts more affinity to the alkyl chains on Abil em 90 polymer and the silicone oil (e.g. DC200/50) improves the consistency of the oil blend.

Example 18

In one aspect of the invention the invention relates to incorporation of a gel particle suspension agarose into an aqueous skin care composition.

Example 18a

Specifically, a composition (shown in Table 4) was made comprising:
1) 19.5% of the suspension of Example 14; and
2) 80.5% of base having a formulation noted in Table 3

TABLE 3

Base formulation

| Ingredient | Function | Wt./Wt. % |
|---|---|---|
| Distilled water | — | ~34% |
| Disodium EDTA | Preservative/chelator | 0.050 |
| Glycerine | Humectant | 3.0 |
| Preservatives | — | 0.7 |
| Polymethylene (20) sorbitan monopalmitate | Surfactant | 2.0 |
| Silicone elastomer (DC 9041) | Particle and silicone volatile | 18.0 |
| Dimethicones 50 cts | | 2.02 |
| Dimethicones 5 cts | | 1.0 |
| DC 245 | Silicone volatile | 16.0 |
| Lilac 100 | Mineral oil/emollient | 0.3 |
| Koba MSP-825 (PMMA)[1] | Sensory modifier | 2.7 |
| Aristoflex AVC ex Clariant[2] | Thickener | 0.483 |

[1]Methylmethacrylate crosspolymer
[2]Ammonium Acryloyldimethyltaurnate/vinylpyrolidone copolymer

TABLE 4

Final formulation of the topical product using Agarose Gel particles suspension of Example 14

| Ingredient | Function | Wt./Wt. % |
|---|---|---|
| Distilled water | — | ~34% |
| Disodium EDTA | Preservative/chelator | 0.050 |
| Glycerine | Humectant | 3.0 |
| Preservatives | — | 0.7 |
| Polymethylene (20) sorbitan monopalmitate | Surfactant | 2.0 |
| Silicone elastomer (DC 9041) | Particle and silicone volatile | 18.0 |
| Dimethicones 50 cts | | 2.59 |
| Dimethicones 5 cts | | 1.0 |
| DC 245 | Silicone volatile | 16.0 |
| Lilac 100 | Mineral oil/emollient | 1.2 |
| Koba MSP-825 (PMMA) | Sensory modifier | 2.7 |
| Aristoflex AVC | Thickener | 0.483 |
| Agarose gel particles (from example 14 suspension) | Sensory modifier | 18.0 |
| Sorbitan monooleate (from example 14 suspension) | Surfactant | 0.03 |

The topical product base was mixed in a standard equipment. The Agarose gel particle suspension from example 14 was then added to the base and mixed until uniform. The final composition is as shown in Table 4

Example 18B

In comparison to example 18A, another topical formulation was prepared as shown in Table 5, which is the same as example 18A, except agarose gel particle suspension was substituted with the same amount of water.

TABLE 5

The topical product made substituting Agarose gel particle suspension with the same amount of water

| Ingredient | Function | Wt./Wt. % |
|---|---|---|
| Distilled water | — | ~52% |
| Disodium EDTA | Preservative/chelator | 0.050 |
| Glycerine | Humectant | 3.0 |
| Preservatives | — | 0.7 |
| Polymethylene (20) sorbitan monopalmitate | Surfactant | 2.0 |
| Silicone elastomer (DC 9041) | Particle and silicone volatile | 18.0 |
| Dimethicones 50 cts | | 2.59 |
| Dimethicones 5 cts | | 1.0 |
| DC 245 | Silicone volatile | 16.0 |
| Lilac 100 | Mineral oil/emollient | 1.2 |
| Koba MSP-825 (PMMA) | Sensory modifier | 2.7 |
| Aristoflex AVC | Thickener | 0.483 |
| Sorbitan monooleate | Surfactant | 0.03 |

The sensory attribute of the inventive composition, example 18a, shown above relative to control (with no agarose), example 18B, and Pond's Fine Pore was evaluated via a sensory panel which demonstrated that the inventive composition was perceived as being more silky than the composition containing no agarose and in parity to the sensory feel of Pond's® Fine Pore.

What is claimed is:

1. A HIPE-gellation process for preparing a highly concentrated, spherical, biopolymer gel particle suspension composition which composition comprises:
   a) an aqueous phase comprising 60 to 99% by wt. of said suspension of spherical biopolymer gel particles;
   wherein average diameter of the particles in the suspension is 1 to 50μ;
   wherein the biopolymer gel particles are formed from the aqueous internal phase of a high internal phase emulsion intermediate (HIPE) product whereby the aqueous internal phase comprises biopolymer and water or polar solvent; and
   b) an oil phase comprising 1 to 40% by wt. of suspension where the oil phase comprises a mixture of oils and surfactants used in formation of said HIPE intermediate and wherein amounts of the oil and surfactants in said HIPE intermediate are as follows:
      (i) 0.1 to 30% by wt. of said HIPE intermediate comprises an oil or mixture of oils suspending said biopolymer particles of (a); and
      (ii) 0.01 to 10% by wt. of said HIPE intermediate product comprises surfactant or surfactants dissolved or dispersed in said oil or oil mixture of (b)(i)
   wherein said surfactant comprises a nonionic surfactant having a hydrophilic-lipophiloc balance (HLB) less than 15;
   wherein said process for forming the suspension composition comprises:
      (A) forming an aqueous solution by dissolving 0.01 to 15% by wt. biopolymer into water and optionally polar solvent, as well as optional water-soluble active, wherein the ratio of said biopolymer to water or polar solvent is 0.01/99.99 to 15/85% by wt., and heating dispersion formed to a temperature of about 60° C. to about 100° C. which is above the gellation temperature of the biopolymer;
      (B) forming an oil solution by dissolving or dispersing 0.01 to 10% by wt. surfactant(s) into 0.1 to 30% by wt. oil or mixture of oils, and heating said solution to a temperature of about 60° C. to about 100° C. which is above the temperature of the gellation temperature of the biopolymer;
      (C) dispersing the biopolymer solution of (A) into the oil solution of (B) at a temperature of about 60° C. to about 100° C., which is above the gellation temperature of the biopolymer in order to form, as intermediate product, a water-in-oil high internal phase emulsion (HIPE) with biopolymer solution as internal phase in the form of small spherical droplets of 1 to 50μ which is suspended in oils found in the continuous oil phase; and
      (D) cooling said HIPE containing biopolymer solution as internal phase to a temperature below the gellation temperature of biopolymer to form gel particle suspension composition defined by (a), (b)(i) and (b)(ii).

2. A process according to claim 1 wherein said HIPE is cooled to form the highly concentrated biopolymer gel particle suspension to a temperature below the gelling temperature of the biopolymer, within the range of 15° C. to 45° C.

3. A process according to claim 1 wherein said oil or oil mixture comprises 1 to 9% by wt. of HIPE.

4. A process according to claim 1 wherein said surfactant or surfactants comprise 0.1 to 2% by wt. of said HIPE.

5. A process according to claim 1 wherein said nonionic surfactant has an HLB of less than 10.

6. A process according to claim 1 wherein said range of particle diameter of the particles is 5 to 40 microns.

7. A process according to claim 1, wherein the biopolymer is selected from the group consisting of carrageenan furcellaren, pectin, alginate, agar, agarose, gellan, glucomannen, galactomannan, xanthan, modified cellulose, gelatin, whey protein and mixtures thereof.

8. A process according to claim 1 wherein said polar solvent is selected from the group consisting of sorbitol, hydroxypropyl sorbitol, glycerine, ethoxylated glycerol, propolylated glycerol, polyalkylene glycols like polyethylene glycol and polypropylene glycol, diethylene glycol, dipropylene glycol, triethylene glycol, 2-ethoxyethanol, hexylene glycol, butylene glycol, hexamatriol.

9. A process according to claim 1 wherein said water soluble actives, if present water soluble colorants and skin beneficial agents selected from the group consisting of glycolic acid, amino acids, glycerine, hydroxypropyl tri ($C_1$ to $C_3$ alkyl) ammonium salts and mixtures).

10. A process according to claim 1 wherein said surfactant is nonionic and comprises linear, branched or cross-linked dimethicone polymers modified with polyether and/or alkyl chain; esters of sorbitan with fatty acids; cremaphor based surfactants; sucrose esters; monoglyceride based surfactants and mixtures thereof.

11. A process according to claim 1 wherein said oil is selected from the group consisting of non-volatile mineral oil, organic oils, silicone oils and mixtures thereof.

12. A process according to claim 11 wherein said organic oil comprises triglyceride.

13. A process according to claim 11 wherein said organic oil comprises an ester of $C_1$-$C_{10}$ carbon of fatty acids with a $C_8$-$C_{24}$ chain length.

14. A process according to claim 1 wherein said combination of oil and surfactant excludes the specific combination consisting essentially of cetyl PEG/PPG-10/1 dimethicone and silicone oil when silicone oil is the only oil used in the preparation of HIPE intermediate.

15. A process according to claim 1 wherein said combination of oil and surfactant excludes cetyl PEG/PPG-10/1 dimethicone and light mineral oil when light mineral oil is the only oil used in the preparation of HIPE intermediate.

* * * * *